(12) United States Patent
Gemmer (10) Patent No.: US 10,548,634 B2
(45) Date of Patent: Feb. 4, 2020

(54) DILATOR

(71) Applicant: Troy Gemmer, El Cajon, CA (US)

(72) Inventor: Troy Gemmer, El Cajon, CA (US)

( * ) Notice: Subject to any disclaimer, the term of this patent is extended or adjusted under 35 U.S.C. 154(b) by 320 days.

(21) Appl. No.: 15/210,824

(22) Filed: Jul. 14, 2016

(65) Prior Publication Data

US 2017/0014161 A1 Jan. 19, 2017

Related U.S. Application Data (60) Provisional application No. 62/192,463, filed on Jul. 14, 2015.

(51) Int. Cl.
| | | |
|---|---|---|
| *A61B 17/42* | (2006.01) | |
| *A61B 17/46* | (2006.01) | |
| *A61D 1/10* | (2006.01) | |
| *A61M 29/00* | (2006.01) | |

(52) U.S. Cl.
CPC .............. *A61B 17/42* (2013.01); *A61M 29/00* (2013.01); *A61M 2210/1475* (2013.01)

(58) Field of Classification Search
CPC .......... A61M 29/00; A61M 2210/1475; A61M 25/0194; A61B 17/42; A61B 17/34
See application file for complete search history.

(56) References Cited

U.S. PATENT DOCUMENTS

| | | | | | |
|---|---|---|---|---|---|
| 1,729,044 | A | * | 9/1929 | Kirk | ............................ A61F 7/12 126/263.05 |
| 1,750,272 | A | * | 3/1930 | Kirk | ........................ A61M 29/00 219/227 |
| 1,873,427 | A | * | 8/1932 | Kirk | ........................ A61M 29/00 606/197 |
| 4,260,570 | A | * | 4/1981 | Ravel | ........................ A61B 17/42 264/46.6 |
| 4,487,209 | A | * | 12/1984 | Mehl | ........................ A61B 10/025 600/567 |
| 5,355,292 | A | * | 10/1994 | Hoftman | .................. F21V 21/403 150/155 |
| 5,540,658 | A | * | 7/1996 | Evans | ........................ A61B 17/42 604/101.04 |
| 5,681,340 | A | * | 10/1997 | Veronikis | .............. A61M 29/00 600/207 |
| 5,858,010 | A | * | 1/1999 | Berry | .................. A61M 3/0262 222/568 |
| 2002/0133128 | A1 | * | 9/2002 | Heller | ................ A61B 17/3421 604/270 |
| 2002/0165489 | A1 | * | 11/2002 | McGuckin, Jr. | .. A61M 25/0662 604/109 |
| 2004/0260327 | A1 | * | 12/2004 | Mueller, Jr. | ........... A61M 29/00 606/191 |
| 2006/0004398 | A1 | * | 1/2006 | Binder, Jr. | ........... A61B 17/3417 606/191 |
| 2007/0043388 | A1 | * | 2/2007 | Greenwood | ........... A61M 29/00 606/193 |
| 2008/0258463 | A1 | * | 10/2008 | Horikawa | .............. F16L 37/113 285/362 |

(Continued)

*Primary Examiner* — Amy R Weisberg
(74) *Attorney, Agent, or Firm* — Donn K. Harms (57) ABSTRACT

A vaginal dilator is provided having a handle which is removably engageable with a base of any one of a plurality of dilators using complimentary connectors connecting the base of each dilator to the handle. Thereby allowing for adjusting the size of the device. A flexible skeletal body may be included within a cavity of the dilator.

14 Claims, 4 Drawing Sheets

(56) References Cited

U.S. PATENT DOCUMENTS

| | | | | |
|---|---|---|---|---|
| 2009/0005635 | A1* | 1/2009 | Zhang | A61H 19/44 600/38 |
| 2014/0155840 | A1* | 6/2014 | Tseng | A61M 31/00 604/257 |
| 2014/0336688 | A1* | 11/2014 | Bacher | A61B 17/00234 606/191 |
| 2015/0066071 | A1* | 3/2015 | Alexander | A61F 5/08 606/199 |
| 2015/0282838 | A1* | 10/2015 | Langdale | H01F 7/0221 606/119 |
| 2016/0331929 | A1* | 11/2016 | Lampropoulos | A61M 25/0097 |
| 2017/0266398 | A1* | 9/2017 | Murray | A61M 13/00 |
| 2018/0071502 | A1* | 3/2018 | Hakim | A61M 29/02 |

\* cited by examiner

DILATOR

This application claims priority to U.S. Provisional Patent Application Ser. No. 62/192,463 filed on Jul. 14, 2015, which is included herein in its entirety by this reference thereto.

FIELD OF THE INVENTION

The device and method herein concerns a dilator for medical uses and procedures requiring such. More particularly, the device herein disclosed concerns a system including one or a plurality of dilator components each adapted at a first end to a common handle. The plurality of inserts can include variable sizes as well as variable flexibility to provide the user a choice for use during such procedures most adapted to their anatomy and progress of treatment.

BACKGROUND OF THE INVENTION

Vaginismus, is the physical or psychological medical condition which affects a person's ability to engage in any form of vaginal penetration. Such can include sexual intercourse, insertion of tampons or menstrual cups, as well as the penetration involved in gynecological examinations (pap tests).

The condition is presumed to be the result of an involuntary vaginal muscle spasm, which makes any kind of vaginal penetration, including sexual intercourse painful or impossible. While there is currently a lack of medical evidence to definitively pinpoint a cause and which muscle is responsible for the spasm, the pubococcygeus muscle, sometimes referred to as the "PC muscle", is most often suggested by medical professionals. Other muscles such as the levator ani, bulbocavernosus, circumvaginal, and perivaginal muscles have also been suggested as a cause or contributing factor to the problem.

A person suffering from vaginismus does not consciously control the spasm. The vaginismic reflex can be compared to the response of the eye shutting when an object comes towards it. The severity of vaginismus, as well as the pain during penetration (including sexual penetration), varies from person to person.

Conventionally, there are products on the market employed to treat this condition. The currently available products employ a graduated set of vaginal inserts for employment in the treatment of vaginismus, various pelvic floor disorders, or to rehabilitate a patient following surgery.

The conventional product can generally be divided into inserts which are flexible or inserts which are rigid. Amongst these two types of products, some employ handles and some do not.

Conventional products which do provide flexible vaginal inserts of various sizes have significant limitations. Such products do not provide handles and are, thus, difficult to grip by the user and subsequently employ. Without handles, it is difficult for a user to communicate pressure to the insert and thereby against muscle and tissue which helps with the rehabilitation process. Additionally, because the insert is generally lubricated for user comfort, the lack of a handle invariably causes the employed lubricant to transfer to the user's hands making a mess, and making it more difficult to grip the dilator insert during use effectively.

Additionally, the flexibility of such conventional inserts, is generally achieved by the employment of thick rubber or silicone to form a solid body or thick wall body of the insert. This construction renders the inserts heavy and stiff. Since with the conventional design, the silicone or rubber material of the body of the insert, must be thick enough to withstand collapse of the sidewalls defining the exterior surface.

This required thick or solid form construction renders these inserts more expensive to manufacture and ship as well as being less flexible than might be desirable by the user. Further, so constructed, the inserts are too thick to nest for shipping thereby making shipping packages larger and more expensive.

Finally, the flexibility of such inserts is generally very limited even though they are sold for this ability. This is because, as noted, the traditional design requiring thick walls, along with a durometer stiffness of the material to maintain structural integrity, severely limits the desirable cushioning for the insert and flexibility.

With regard to insert products which are formed of hard materials or inflexible materials, in addition to lacking desirable flexibility and cushioning, other aspects are lacking. Many such devices in this configuration either don't have a handle, or if they do have a handle, the handles provide a very weak frictional engagement which causes the insert to dismount too easily. As can be discerned, such causes a patient user significant distress and frustration during use.

Further, a number of available products using a handle engageable to the insert, employ a handle having projecting annular ridge portions, to accommodate different sized insert mounting. However, such devices leave projecting ridge portions, unused by other inserts, exposed which act like uncomfortable projections which scrape or bind upon the patient's skin and soft tissues during use.

Finally, many of the products of both types noted above have poor ergonomic configurations and shape at the distal end employed for insertion. They lack an egg or curved shape allowing for more comfortable communication during insertion and additionally lack a tapering of the insert from a narrower distal end to a wider base to allow for a more gradual insertion process.

As such, there exists an unmet need for a dilation device and method which remedies the noted shortcomings in the current art. Such a system should provide an easily gripped handle having a dilator mount at one end. The dilator mount should provide an engagement system which will engage any of a large plurality of different insert components with the same mount. Once an insert is engaged, no ridges or gaps would be present at the engagement point of the insert to the handle and only a smooth surface should be presented which eliminates the discomfort noted in current systems. Finally such a system should provide dilators engageable to the common handle which vary in size, and vary in overall stiffness to allow for inserts which will bend during use. This bending should be provided by a flexible skeletal system covered by soft polymeric material to provide maximum flexibility with maximum comfort to the user.

The forgoing examples of related art and limitations related therewith are intended to be illustrative only, and not exclusive, and they do not imply any limitations on the invention described and claimed herein. Various other limitations of the related art will become apparent to those skilled in the art upon a reading and understanding of the specification below and the accompanying drawings.

OBJECTS OF THE INVENTION

One object of the instant invention is to provide a handle engaging insert for vaginal or other insertion which securely engages with a single handle and in doing so, eliminates projections or other surface areas which cause discomfort during use.

Another object of this invention is to provide such a handle engaged insert system which provides a plurality of different sized inserts for use with a handle.

Another object of this invention is to provide such a handle engaged insert system which provides a plurality of different inserts of varying flexibility which are engageable to the handle.

These and other objects, features, and advantages of the present device and method, as well as the advantages thereof over existing prior art which will become apparent from the description to follow, are accomplished by the improvements described in this specification and hereinafter described in the following detailed description which fully discloses the invention, but should not be considered as placing limitations thereon.

SUMMARY OF THE INVENTION

In accordance with the purposes of the disclosed device and method as embodied and broadly described herein, there is provided a dilator system especially well configured for use as a vaginal dilator. While described as such herein, the disclosed handle and engaging dilator system herein could also be employed for other dilating purposes such as an anal or urinary dilator with the dilator component adapted for such use.

The system herein features an ergonomic handle having a mount at a first end, which extends to a distal end having an enlarged diameter tip. A gripping area is positioned between the mount and the distal end which is adapted for gripping by the hand of a user.

The gripping portion of the handle is preferably formed with a soft skin for the user to grip upon comfortably. The enlarged portion at the distal end helps prevent the user's hand from slipping from the handle during use which is especially possible if lubricant is being employed concurrently.

The mount is configured for a twist and lock engagement between an annular base of the dilator and the mount on the end of the handle. At least one projection extending from the circumference of the base of the dilator, is configured for translation into a complimentary shaped recess on a mating surface of the mount. Engagement between the dilator base and the handle is accomplished by positioning the projections upon the base of a dilator, into the complimentary recesses. The projections thereafter slide into a slot formed in the mount whereupon a twisting of the dilator slides the projection into a locked engagement with the slot. This engagement leaves the smooth surface at the base of the dilator and the dilator itself, as the only surfaces contacting the flesh of the user during use.

The system herein provides a plurality of dilators in a kit for the user, and each of the provided dilators is configured with a base adapted for removable engagement with a handle such as with at least one projection which is configured for the twist lock engagement noted above with the mount of the handle.

While the base of each dilator is configured for the twist lock engagement with the mount of the handle, the dilators projecting from the base, can vary in width, length, and flexibility. Thus, a single handle may engage rigid dilators or flexible dilators, and the size of each type may vary in length and girth. Thus, great utility is provided to the user by being able to engage to a single handle mount, a large plurality of dilators.

The dilators, be they rigid or flexible, may have an axial cavity within the sidewall defining the exterior shape of the dilator extending from the base thereof. The void within the interior axial cavity significantly reduces shipping and reduces material use. Further, when a sequential sized group of dilators is provided to the user, the smaller diameter dilators may be nested sequentially within slightly larger diameter dilators. This nesting ability reduces the size of the device for shipment and tends to keep all the parts of the kit together and engaged.

A particularly preferred mode of the dilator includes a skeletal body or structure positioned in a contact with an interior surface of the sidewall forming the dilator extending from the dilator base. The skeletal structure can be varied for flexibility by varying gaps between skeletal sections.

The skeletal structure is covered with a softer, flexible polymeric material on at least the exterior of the dilator, and preferably the interior also. Both sides of the sidewall are preferable, because it has been found the adherence of the polymeric skin to the exterior of the sidewall forming the dilator is enhanced by the polymeric material being placed internally and communicating with the external skin of the dilator through gaps in the skeletal system.

As noted, the plurality of dilators where each is engageable to the same handle, can include a common base, from which the annular sidewall forming the dilator projects in different widths and/or lengths from the base. The projecting sidewall preferably narrows as it approaches the distal end to form a distal tip which is egg shaped. This configuration presents a narrower width of the dilator for use during insertion which slowly widens providing user comfort.

With respect to the above description of the dilator herein, before explaining at least one preferred embodiment of the herein disclosed device and system detail, it is to be understood that the invention is not limited in its application to the details of construction and to the arrangement of the components in the following description or illustrated in the drawings. The device and method herein described and disclosed in the various modes and combinations is also capable of other embodiments and of being practiced and carried out in various ways which will be obvious to those skilled in the art. Any such alternative configuration as would occur to those skilled in the art is considered within the scope of this patent. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other dilator systems. It is important, therefore, that the claims be regarded as including such equivalent construction and methodology insofar as they do not depart from the spirit and scope of the present invention.

BRIEF DESCRIPTION OF DRAWING FIGURES

The accompanying drawings, which are incorporated herein and form a part of the specification, illustrate some, but not the only nor exclusive examples of embodiments and/or features of the disclosed device. It is intended that the embodiments and figures disclosed herein are to be considered illustrative of the invention herein, rather than limiting in any fashion.

In the drawings.

DETAILED DESCRIPTION OF THE INVENTION

Now referring to drawings in FIGS. 1-10, wherein similar components are identified by like reference numerals, there is seen the device 10 which may be employed in the method herein.

As noted above, in FIG. 1 is depicted the dilator device 10 herein, formed of a handle 12 engaged with the first end of a dilator 14. The dilator 14 is preferably formed in a cylindrical shape at the first end having a base 20 thereon configured with complimentary connectors to engage the first end of the handle 12. At the distal end of the dilator 14 opposite the first end, the dilator 14 has a spherically blunted cone shape.

Figures 1, 2:
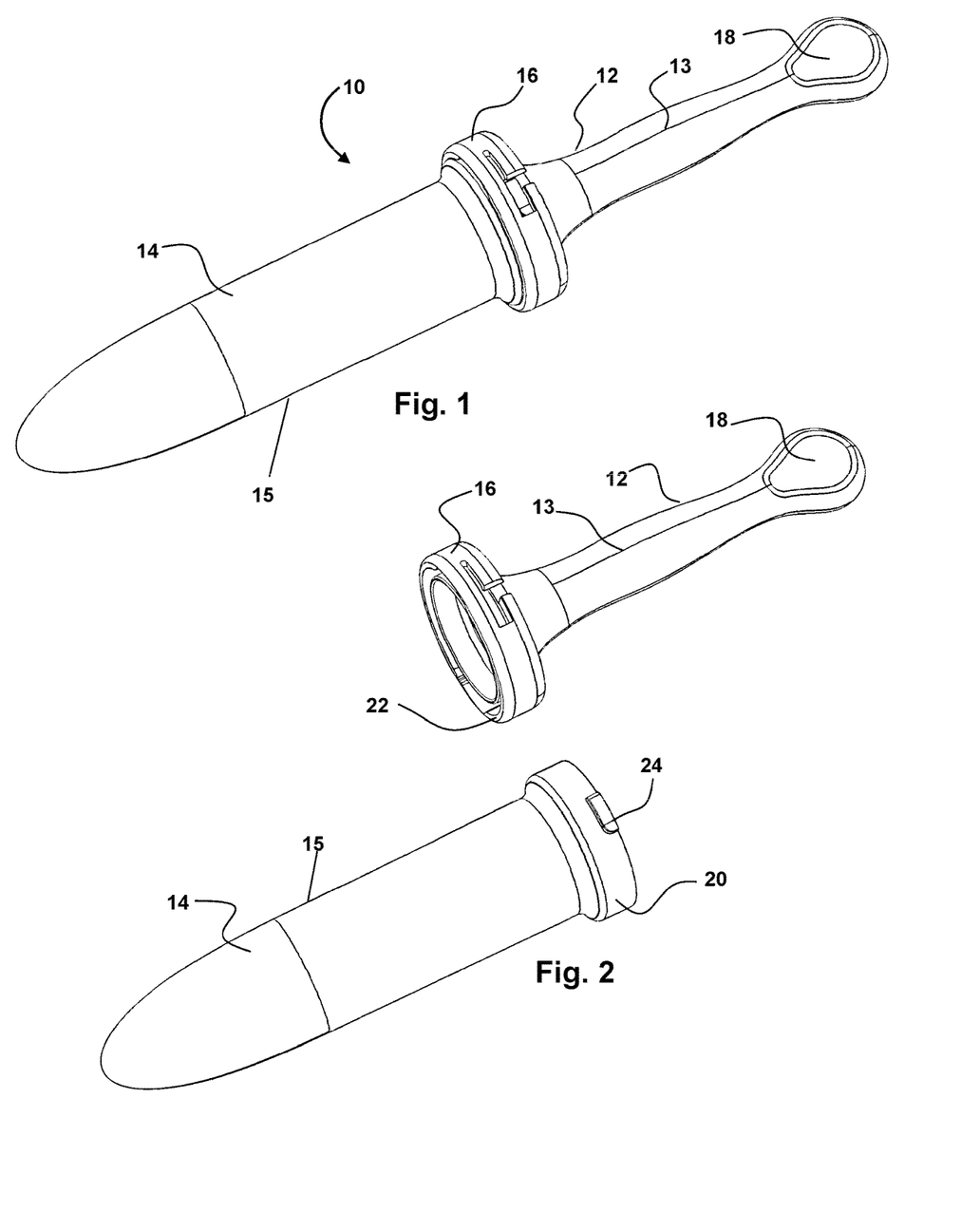
FIG. 1 depicts the dilator system herein showing the dilator removably engaged with a base formed on the handle.
FIG. 2 shows an exploded view of FIG. 1 showing the base of the dilator configured for a complimentary engagement into the mount of the handle using a twist lock engagement.

The dilator 14 and the handle 12 are connectable in a removable engagement with the complimentary connectors with the first end of the dilator 14 removably engageable with a mount 16 positioned on the first end of the handle 12 opposite a widened portion 18 of the handle at or adjacent a proximal end opposite the first end of the handle 12. Complimentary connectors positioned on both the first end of the dilator 14 and the first end of the handle 12 render the dilator 14 removably engageable with the handle 12.

The widened portion 18 as noted has a cross section which is wider than that of a central area 13 of the handle 12. This widened area 18 may be planar or may have a slight recess depending into the handle 12 on opposing sides of the handle 12. This widened area is particularly preferred at the proximal end of the handle 12 as it is configured for employment during gripping of the central area 13 of the handle 12 by the user. This is because the widened portion 18 forms a stop to prevent a hand of the user from sliding off the proximal end of the handle 12, in the direction toward the widened portion 18 when pulling the handle in a direction toward the proximal end.

The handle 12 has a mount 16 at the first end configured to be complimentary to the shape of the base 20 at the first end of each dilator 14, and to include complimentary connectors on each of the dilator 14 and the handle 12 to form a removable engagement therebetween. Thus, a single handle 12 so configured will operatively engage with each of any of a plurality of dilators 14, which may be provided in a kit such as in a combination of the dilators 14 of FIGS. 8-10 which are of differing configurations but have the same base 20 size and complimentary connectors.

Disengagement of the two components can be seen in FIG. 2 which shows an exploded view of the components of FIG. 1 in the engaged configuration. As depicted in FIG. 2, the base 20 at the first end of the dilator 14 from which the projecting portion 15 of the dilator 14 extends, is configured for the removable engagement into a facing surface 22 the mount 16 on the first end of the handle 12. The projecting portion 15 has a length and width extending from the base 20 to the distal end which curves to a rounded point.

Complimentary connectors on each of the base 20 and the handle 12 form the removable engagement. These complimentary connectors may be provided by projections 24 extending from the circumference of the base 20 of the dilator 14, configured to slide into complimentary recesses 26 of the mount 16 of the handle 12. Once so situated, a twisting of one or both of the handle 12 and dilator 14 will translate the projections 24 into locked positions 28 within a slot formed in the mount 16 communicating with the recesses 26. Twisting the opposite way will unlock the engagement and allow for separation.

Figure 3:
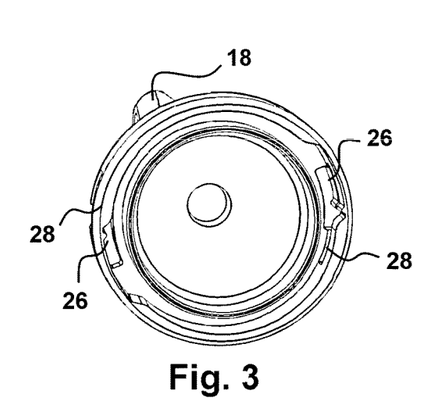
FIG. 3 depicts an overhead view of the facing surface of the mount of the handle showing recesses complimentary in shape to the projections on the base of the dilator for insertion therein.
Figure 4:
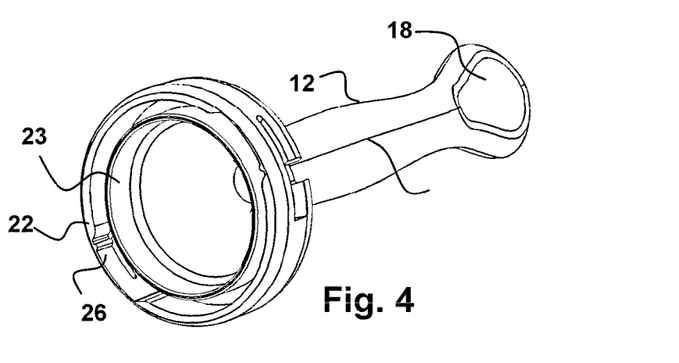
FIG. 4 shows a perspective view of the handle of FIG. 3, showing the facing end recesses communicating with an internal passage allowing a circular translation of the projections on the base of the dilator.

FIGS. 3-4 show views of the facing surface 22 of the mount 16 of the handle 12 showing recesses 26 being complimentary in shape to the projections 24 on the base 20 of the dilator 14 for insertion therein whereby they may twist to a locked engagement. The removable engagement of a first end of the dilator 14 to the handle 12 may simply employ these cooperative connectors shown as projections 24 and recesses 26, to form such a removable engagement, and of course they may be reversed in positioning.

Figure 5:
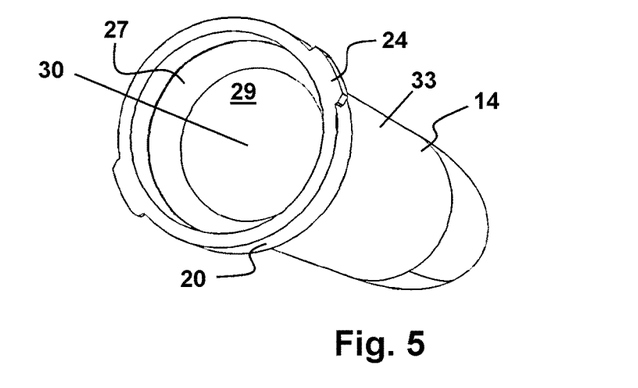
FIG. 5 shows the axial cavity formed within each dilator communicating with a passage through the base of each dilator additionally showing the projections extending from the circumference of the base.

Additionally preferred, as a part of this removable engagement of complimentary connectors, as shown in FIG. 4, is an annular projection 23. This annular projection 23 may have an exterior diameter equal to or just slightly larger than a contact with a circumferential portion of the interior angled surface area 27 adjacent a first end of the dilator 14 as shown in FIG. 5, or it could be slightly smaller in diameter if the annular projection 23 has an angular projection slightly outward from the center axis shown as line 31 in FIG. 6, such that the annular projection 23 contacts the interior angled surface 27 of the dilator 14.

The dilator 14 may be formed with the interior surface 29 of the sidewall 33 extending to a straight or liner connection to the base 20, and the annular projection 23 may be sized circumferentially to contact a straight or linear interior surface 29 circumferential portions of the interior surface 29, in frictional contact or biased contact, in another mode of the dilator 14.

However, experimentation has shown that a contact of a portion of a leading edge of the annular projection 23 with a circumferential portion of the interior surface 29, either linear and parallel to the direction of the annular projection 23, or formed as an angled surface area 27 at a first end of dilator 14, in its connection to the base 20, allows for a better contact and removable engagement. Further, this linear contact or a more biased contact of the annular projection 23 provides significant increased stabilization of the base 20 of the dilator 14 from dismounting from the mount 16 and the handle 12. Consequently this annular projection 23 is preferred present and in a configuration which forms a contact with either the circumferential surface of the interior surface 29, either parallel to a linear circumferential surface, or more preferably with the circumferential surface of contact being an angled surface 27 of the base 20 of the dilator 14.

Further, if the annular projection 23 is formed of pliable material, such as a polymeric material, it has been found the circumference of the annular projection 23, if formed to angle outward or away from the axis 30, and toward the circumference of the angled surface 27, will become compressed against a circumferential portion of the interior surface 29 which in this case is shown as the angled surface 27. Such a compressed contact provides an biasing force from the projection 23 angling outward away from the axis 31 of the axial cavity 30 and toward the circumferential portion of the interior surface shown as the angled surface 27. Thus, a configuration of the projection 23 to form a biased removable engagement with the circumferential portion of the interior surface 29 such as with the angled surface 27 of the dilator 14, as part of the removable engagement of the handle 12 to the dilator 14, enhances that engagement to prevent dismounts of the dilator 14 therefrom.

As can be seen in FIG. 5, a removably engageable connection between the handle 12 and the dilator 14 may be provided and, as noted herein, is preferred. This removably engageable connection can be provided by the projections 24 which extend from the circumference of the base 20, and are positioned and configured to mate with the recesses 26 in the facing surface 22 of the mount 16 on the first end of the handle 12.

Also shown is the hollow axial cavity 30 within the formed dilators 14 herein surrounding an axis. A projecting portion defined by the exterior of the circular sidewall 33, extends from the base 20 toward the distal end of the dilator 14 having the axial cavity therein. For modes of the device 10 with sequentially larger diameter dilators 14, the smaller dilators 14 in the set can nest into these axial cavities 30. The circumferential portion of the interior wall 29 which contacts the projection 23 is also shown as the angled surface 27 in FIG. 5. This angled surface 27 extends in an angle from a narrower cross section closer to the first end of the dilator 14 toward a wider cross section closer to the distal end of the dilator 14.

Figures 6, 6A:
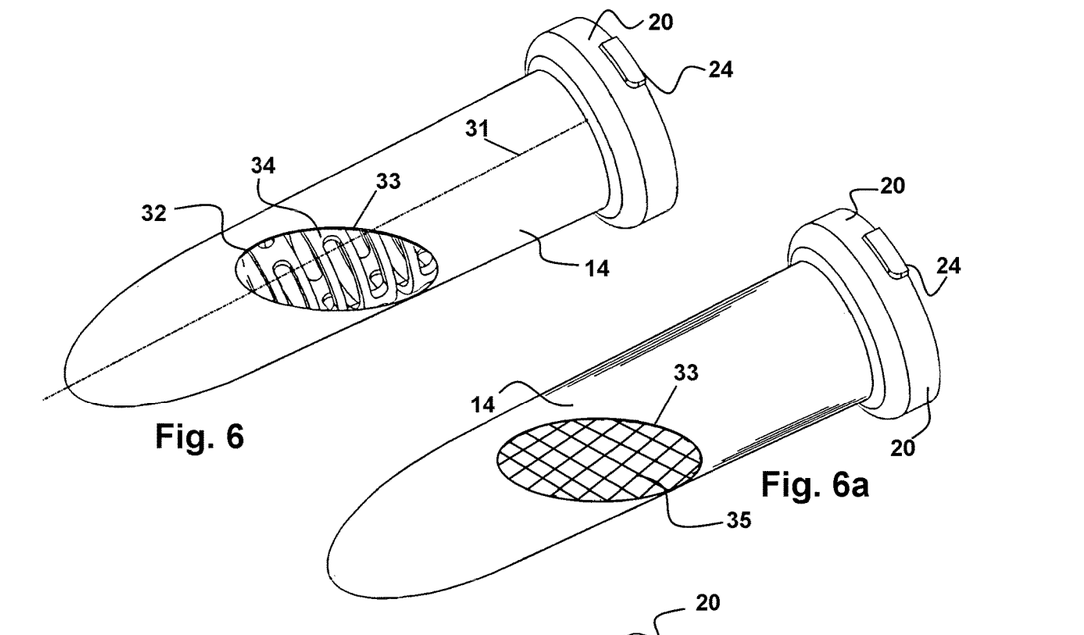
FIG. 6 depicts a mode of the dilator having a flexible skeletal system formed within the sidewall defining the axial cavity of the projecting portion of the dilator.
FIGS. 6a-6b depict the dilator similar to that of FIG. 6, but with differing skeletal systems positioned within the axial cavity.
Figures 6B, 7:
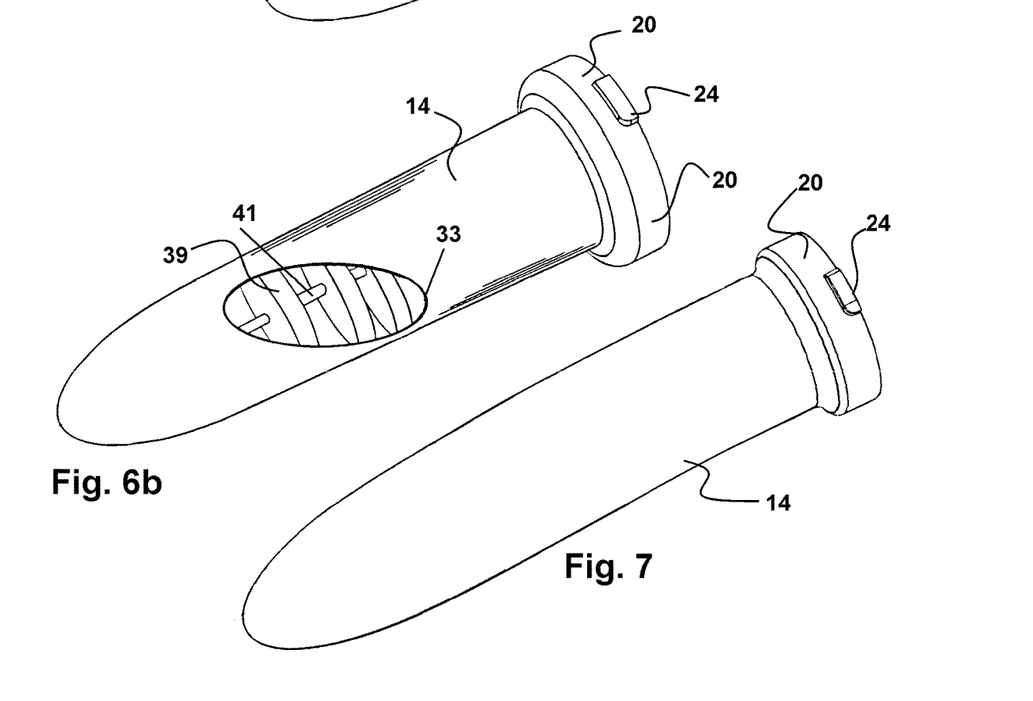
FIG. 7 shows the device of FIG. 5 depicting a slight flexure of the projecting portion of the dilator allowed by the elastic polymeric material coating the exterior of the flexible skeletal structure.

Shown in FIGS. 6-6b are especially preferred modes of the dilator 14 of the device 10 herein. Depicted is a flexible dilator 14 having a circumferential skin 32 defining the exterior of the projecting portion formed by the projecting sidewall 33, covering an axial projecting skeletal body 34 engaged against the sidewall 33 surrounding an axial cavity 30. The skeletal body 34 is preferably formed of a flexible polymeric material or silicone material or other material which is flexible, such that the skeletal body 34, will deflect when pressure is imparted to a side surface of the sidewall 33.

The skin 32 defined by the sidewall 33 covering the engaged skeletal body 34 is a soft and elastic polymeric material which will adhere to or compressively engage the skeletal body 34, and which will stretch and contract to its original size and position. This allows the dilator 14 to accommodate flexing to a curve during use and subsequently returning to its linear configuration.

The skeletal body 34 is preferably formed in a structure and of the noted flexible material accommodating such a flexure to a curve and return to a linear configuration. A honeycomb structure as shown in FIG. 6 has shown to work well, as does a flexible skeletal body 34 formed of diagonally engaged members 35 which are flexible an formed in their diagonal engagement in a shape mirroring the shape of the interior cavity of the dilator 14, and of a size to contact the interior surface of the sidewall 33, shown in FIG. 6a.

Another mode of formation of this flexible skeletal body 34 which works well to support the sidewall 33 to maintain the smooth and curved shape of the skin 32 of the dilator, is shown in FIG. 6b, where sequentially positioned disks 39 having successively smaller circumferences are axially engaged with a flexible member 41 extending along the axis 31 of the dilator 14. In this mode, the respective circumference of each sequentially placed disk 39, is in contact with an interior surface 29 (FIG. 5) of the sidewall 33, and flexure of the member 41 allow the skin 32 formed by the sidewall 33 to move between a curved configuration and linear configuration.

The depiction in FIG. 7, shows the dilator 14 of FIG. 6, fully skinned, and flexing to place the distal tip off center from the axis depicted in dotted line. Of course the flex and curve of any such dilator 14 with a skeletal sidewall, is only limited by the amount of flex and/or elasticity of the material forming the skeletal structure 34 and that of the skin 32 and the depiction showing a slight deflection is not to be considered limiting.

Figure 8:
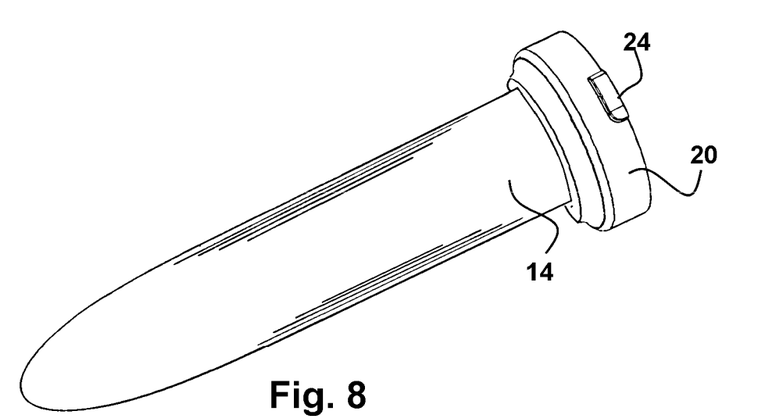
FIGS. 8-10 show differing sized dilators with the same removable engagement to a single handle and could be provided as a kit of dilators each having a sequentially larger cross section or circumference of the projecting portion of the dilator thereby allowing insertion into a nesting storage configuration.
Figure 9:
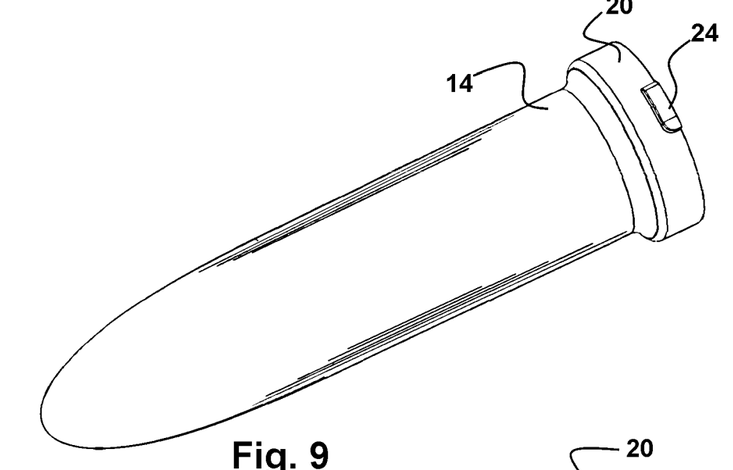
Figure 10:
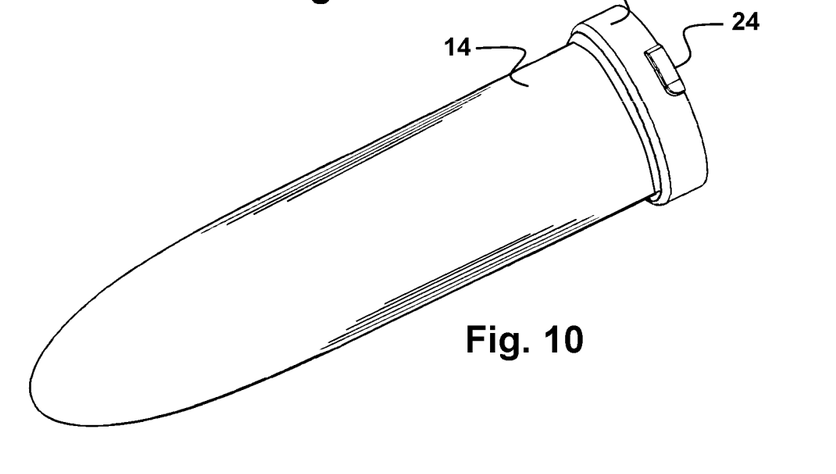

Finally, FIGS. 8-10 depict an example of the dilators 14 of the device 10 being provided in a plurality of dilators 14 in a kit of dilators 14 wherein each has a sequentially larger diameter or circumference or length of the projecting portion 15, from the others. As depicted, the dilator of FIG. 8 is smaller than that of FIG. 9, and could nest within the axial cavity 30 of the dilator of FIG. 9. The dilator 14 of FIG. 9, likewise is smaller than that of FIG. 10, and the dilator of FIG. 9 could nest within the axial cavity 30 of the dilator 14 of FIG. 10, along with the coaxially positioned dilator 14 of FIG. 8.

As noted, any of the different configurations and components can be employed with any other configuration or component shown and described herein. Additionally, while the present invention has been described herein with reference to particular embodiments thereof and steps in the method of configuring the device to user choices, a latitude of modifications, various changes and substitutions are intended in the foregoing disclosures, it will be appreciated that in some instance some features, or configurations, or steps in formation of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

Further, the purpose of any abstract of this specification is to enable the U.S. Patent and Trademark Office, the public generally, and especially the scientists, engineers, and practitioners in the art who are not familiar with patent or legal terms or phraseology, to determine quickly from a cursory inspection the nature and essence of the technical disclosure of the application. Any such abstract is neither intended to define the invention of the application, which is measured by the claims, nor is it intended to be limiting, as to the scope of the invention in any way.

What is claimed is:

1. A dilator apparatus, comprising:
a handle having a first end and having a proximal end opposite said first end;
a mount, said mount having a first end connected to said first end of said handle and having a second end including a distal facing surface opposite said first end thereof;
a cylindrical dilator defined by a sidewall, said dilator having an annular projecting portion defining an annular base at a first end, said annular base surrounding an opening to an interior cavity defined by an inner surface of said sidewall of said dilator surrounding an axis running therethrough, said dilator having a distal end opposite said first end of said dilator;
an exterior surface of said sidewall of said dilator being planar and coaxially surrounding said axis, said exterior surface having a first circumference extending from said annular base toward said distal end of said dilator and defining a projecting portion of said dilator with said planar exterior surface running uninterrupted between said annular base and a point adjacent said distal end of said dilator;
a narrowing of said first circumference from said point adjacent said distal end of said dilator, for a distance extending to said distal end of said dilator, defining a spherically blunted cone shape portion of said dilator at said distal end of said projecting portion;
said annular projecting portion of said dilator having an exterior surface defining a second circumference of said annular base, said second circumference being larger than said first circumference, said annular base sized for insertion into an annular recess depending into said distal facing surface of said mount; and
complimentary connectors comprising projections extending from a circumference of said annular base of said dilator configured to slide into complimentary receiving recesses within said annular recess and said distal facing surface of said mount.

2. The dilator apparatus of claim 1, whereby said complimentary connectors further comprise projections sized to slide into a recessed engagement within said complimentary receiving recesses positioned on said distal facing surface of said mount in a communication with said annular recess depending into said distal facing surface of said mount;
said projections in said recessed engagement moveable to locked positions within said receiving recesses by a twisting of said dilator in a first direction; and
said projections removable from said locked positions by a twisting of said dilator in a second direction opposite said first direction, whereby said dilator can be disengaged from said handle.

3. The dilator apparatus of claim 2 wherein said annular recess is defined by an inner and outer annular wall and said inner wall further comprises:
an annular projection extending from said distal facing surface of said mount; and
said annular projection having an exterior circumference sized to contact said dilator at an annular portion of said inner surface of said sidewall at said opening to the interior cavity.

4. The dilator apparatus of claim 3 wherein said annular projection is formed of pliable material, and said exterior circumference of said annular projection is sized to contact and deflect against said annular portion of said inner surface of said sidewall at said opening to said interior cavity thereby forming a biased contact between said annular projection and said inner surface of said sidewall.

5. The dilator apparatus of claim 4 wherein said annular portion of said inner surface of said sidewall at said opening to the interior cavity is angled from a smaller cross section of said interior cavity, closer to said distal end of said dilator, to a larger cross section of said interior cavity closer to said first end of said dilator.

6. The dilator apparatus of claim 3 wherein said annular portion of said inner surface of said sidewall at said opening to the interior cavity is angled from a smaller cross section of said interior cavity, closer to said distal end of said dilator, to a larger cross section of said interior cavity closer to said first end of said dilator.

7. The dilator apparatus of claim 3 further comprising:
a skeletal body engaged against said interior surface of said sidewall within said interior cavity; and s
said skeletal body formed of a flexible material.

8. The dilator apparatus of claim 2 further comprising:
said sidewall being flexible;
a skeletal body engaged against said interior surface of said sidewall within said interior cavity;
and said skeletal body formed of a flexible material.

9. The dilator apparatus of claim 1 further comprising:
said sidewall being flexible;
a skeletal body engaged against said interior surface of said sidewall within said interior cavity; and
said skeletal body formed of a flexible material.

10. The dilator apparatus of claim 9, wherein said skeletal body comprises a honeycomb structure.

11. The dilator apparatus of claim 9 wherein, said skeletal body comprises diagonally engaged members.

12. The dilator apparatus of claim 9, wherein said skeletal body comprises sequentially positioned disks.

13. The dilator apparatus of claim 1 wherein said proximal end of said handle comprises a block having a cross section wider than a cross section of a central area of said handle positioned between said block and said first end of said handle; and
said block preventing slippage of a hand of a user therefrom in a direction toward said proximal end of said handle.

14. The dilator apparatus of claim 1 wherein said cylindrical dilator is one of a plurality of said cylindrical dilators in a kit of said cylindrical dilators;
each of said plurality of cylindrical dilators having a said base engageable to a single said handle; and
each of said plurality of said cylindrical dilators having a differing size of said first circumference at said annular base and extending therefrom to said spherically blunted cone shape at said distal end of said projecting portion, wherein said cylindrical dilators from said plurality having a respective said first circumference of a first size which is smaller, are insertable to a nesting position within a respective said interior cavity of said cylindrical dilators from said plurality which are larger than said first size, whereby a user may choose any of said plurality of said cylindrical dilators from said kit and removably engage it to said handle.

* * * * *